Feb. 12, 1952 M. O. AHRENS Plant Pat. 1,072
GARDENIA PLANT
Filed March 10, 1950
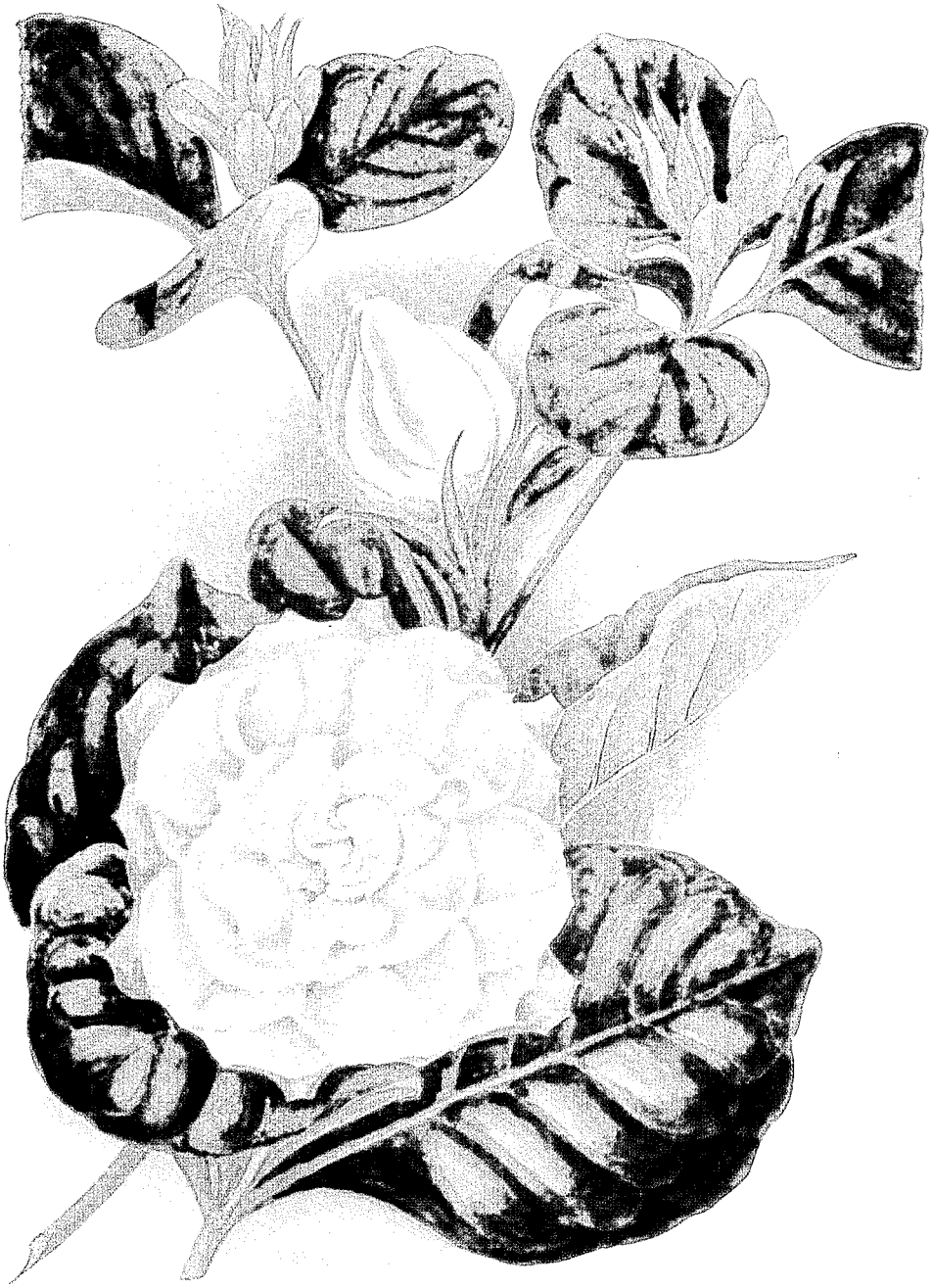
WITNESS
Addison J. Avery
INVENTOR
Melvin O. Ahrens,
Wilkinson, Huffly, Byron, & Hume
ATTYS.

Patented Feb. 12, 1952

Plant Pat. 1,072

UNITED STATES PATENT OFFICE 1,072

GARDENIA PLANT

Melvin O. Ahrens, Crystal Lake, Ill.

Application March 10, 1950, Serial No. 148,980

1 Claim. (Cl. 47—60)

The present discovery relates to an improvement in gardenia plants. The new variety in question is a sport of the variety "Belmont," which sport was discovered by applicant in the month of January, 1948 in applicant's greenhouses at Crystal Lake, Illinois. Asexual reproduction of the newly discovered plant was made at Crystal Lake, Illinois, by taking cuttings in 1948 from the parent plant. Two mature nodes were taken to each cutting of approximately 1½ inch and such cuttings were placed in a sand rooting medium with bottom heat. The new variety has been carefully developed and improved since the growing of the original plants and approximately seventy-two (72) plants grown from cuttings therefrom and from subsequent cuttings, are now in flowering production.

Among the most distinguishing characteristics of the new variety in question are that the plant grows much more slowly than the "Belmont" variety (plant Patent No. 93), such slow growth being advantageous to commercial gardenia growers because the flowers are not normally picked with a stem. Fast growing varieties, on this account, often become unruly in a very short time in greenhouse culture. An additional distinguishing characteristic of great importance is that the plant has a very broad, rounded, dark green leaf, as distinguished from the narrow, oblong leaf of the "Belmont" plant, and other varieties of gardenia plants.

A further distinguishing characteristic is that the bud of the plant is short and thick, whereas the bud of the parent variety is long and narrow. This short, thick bud when opening, unfolds very much like a rose, the open flower resembling an open rose also. The flower normally ranges in size from approximately 3½ to 5½ inches, and develops much more slowly than the flower of the parent "Belmont" variety.

Still another distinguishing characteristic is the full double form of blossom with an unusually large number of petals, particularly at the center of the flower. Apparently because of this unusually large number of petals, on full maturity this newly discovered variety does not have an open center as is clearly apparent in the accompanying drawing and as stated above, resembles an open rose. The slow development of the flower referred to above is also apparently related to the fact that the blossom contains an unusually large number of petals having a dense distribution at the center of the flower.

The structure of the center of the flower at full maturity as just described is particularly desirable in that at no time does the blossom show a black center as is characteristic of the parent variety. This in turn greatly increases the time period in which flowers suitable for commercial use may be cut from the plant.

An additional distinguishing characteristic of the new variety which is the subject matter of this discovery is that its fragrance is not overwhelming, as in most other varieties of gardenia, but it has a sweet and gentle odor similar to that of the wild variety of Cape jasmine. In addition, the petal is very heavy, with extreme substance, and gives the appearance of being waxed. The petals are unusually large and reflexed, giving the blossom unusual depth as well as a large diameter.

The original illustration accompanying this application discloses typical flowered branches of the new variety, particular attention being given to the shape of the leaves, the shape of the bud, and the formation of the flower.

The following is a detailed description of the plant and flower of the new variety which is the subject matter of this application.

*The plant*

Parentage: Sport of Belmont variety.

Classification: *Gardenia grandiflorum.*

Form: Exceptionally heavy growth which makes plant very bushy; the nodes or distance between the sets of leaves are much shorter than parent Belmont variety.

Growth: General growing habits much slower than the Belmont and Hadley varieties; very sturdy and stocky growing plant; unusually large number of branches.

Foliage: Leaves are generally oblong, as in parent, but much more rounded at the extremities; length of Belmont leaf and new variety both approximately 5 to 5½ inches; width of Belmont leaf approximately 2½ to 2¾ inches, whereas width of leaf of new variety approximately 3¼ to 3¾ inches; the texture is much heavier; the color of the upper surface of the leaf is black green, and the lower surface of the leaf light green.

Wood: Heavy structure, sturdy and strong.

*The flower*

Blooming habit: Heavy production January through July; blossoms much lighter the remaining months of the year.

Bud: Of a heavy structure; rounded at the rib; short and stubby.

*Size.*—2½ to 3 inches.

*Form.*—Tapered but unusually round.

*Color.*—Light green.

*Sepals.*—1 to 1½ inches.

*Calyx.*—6 sepals.

Blossom:

*Size.*—Large; 3½ to 5½ inches in diameter.

*Form.*—Full double, consists of: three rows each of six large petals; three additional rows of six petals each, diminishing in size toward the center of the open flower. The petals are reflexed, adding to depth of flower and giving the flower the appearance of an open rose. Petals heavy, with much substance.

*Color.*—Light creamy white; when opening petals have a green strip on left under side; upon maturity this fades, leaving the petal totally white.

*Petals.*—Very heavy and substantial; large and reflexed.

*Fragrance.*—Similar to Cape jasmine; very sweet and appealing.

The color designations according to A Dictionary of Color, by Maerz and Paul, are as follows:

| Section | Plate | Letter | Number |
|---|---|---|---|
| Body of flower | 17 | A | 1 |
| Center of flower | 9 | H | 1 |
| | 9 | shading into D | 3 |
| Main Leaf | 24 | A | 12 |
| Under side of main leaf | 22 | L | 6 |
| Small leaves | 21 | L | 6 |

What is claimed is:

The new and useful variety of gardenia plant substantially as herein shown and described, characterized particularly by its slow but very heavy growth; its stocky and bushy appearance; its broad, dark green leaves, with exceptionally rounded extremities; its short, thick, rounded buds which unfold like a rose; its very full blooms of light creamy white resembling an open rose; its large, reflexed, very heavy petals of extreme substance having a waxed appearance and a green strip on the left under side, which strip fades upon maturity; the large number of petals in the blooms, particularly at the center thereof; the highly symmetrical and closely spaced distribution of the petals; and its sweet and gentle fragrance similar to that of the wild variety of Cape jasmine.

MELVIN O. AHRENS.

REFERENCES CITED

The following references are of record in the file of this patent:

UNITED STATES PATENTS

| Number | Name | Date |
|---|---|---|
| Pl. Pt. 989 | McLellan et al. | Nov. 21, 1950 |